United States Patent [19]

Ison

[11] Patent Number: Plant 7,265

[45] Date of Patent: Jul. 10, 1990

[54] SWEET JENNY

[76] Inventor: William G. Ison, Rte. 1, Box 19, Hwy. 19, Brooks, Ga. 30205

[21] Appl. No.: 166,245

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety F11-2-2 and the pollen parent variety F12-12-1 to produce an improved variety of muscadine grape.

1 Drawing Sheet

DESCRIPTION OF THE VARIETY

A cross between F11-2-2 and F12-12-1.

The primary objective of the breeding was to produce an improved variety of muscadine grape; the fruit to be large, sweet, bronze, dry scar for long shelf life, female; the fruit to have superior characteristics than either of its parents. Its characteristics include even ripening fruit with high acid, and the plant being vigorous and productive.

In comparison with both the seed and pollen parent, the new variety is not similar to parents, one parent being red. The fruit of this plant is much larger, sweeter, more dry scar, higher quality than either parent. The present variety yields on the average of 5 to 7 tons per acre in tests conducted at Ison's Nursery & Vineyards, Brooks, Ga. The fruit from this plant has an excellent flavor.

Asexual reproduction of the new variety either by softwood cutting or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit if ripe and ready for picking and as depicted in color as nearly true as it is resonably possible to make the same in color illustration of the characters.

The following is a detailed description of the new variety:

Species: *Vitis rotundifolia.*
Type: Vine.
Seed parent: F11-2-2.
Pollen parent: F12-12-1.

Propagation: Holds its characteristics through succeeding propagation by either layering or by softwood cuttings.
Locality where grown: Brooks, Ga. 30205.
Fruit borne: Usually in clusters of 3 to 12 berries per cluster.
Fruit size: Large, bigger in size than either parent, appx. 1 and ¼" diameter.
Fruit color: Greyed Orange, 165B Fan 4 Royal Horticultural Society London, England.
Sugar content: 24% soluble solids average.
Fruit shape: Round.
Seed: Average diameter ⅛ inch, average seed per berry 2.65.
Fruit pulp: Color: Greyed Green, 194C, Royal Horticultural Society. Fan 4, London, England.
Consistency: Medium soft and juicy as compared to most muscadine vines.
Skin: Medium thick.
Foliage: Leaf color Green Group 136B Fan 3 Royal Horticultural Society, London, England. Leaf size and shape similar to most muscadine varieties.
Reproductive organs:
*Pistillate.*—Not self pollinating. Note: This is a female variety which can be reproduced from cuttings but when planted will not pollinate other varieties.
Growth habits: Requires Support, very productive and vigorous, dry scar, mid to late season.
Canes: Medium.
Maturity date: Usually ripens about September 20 at Brooks, Ga.
Diseases: Tolerant to Muscadine diseases.

This description was made from a muscadine vine grown at Ison's Nursery & Vineyards, Brooks, Ga.

I claim:

1. The new and distinct variety of grape plant as described and illustrated.

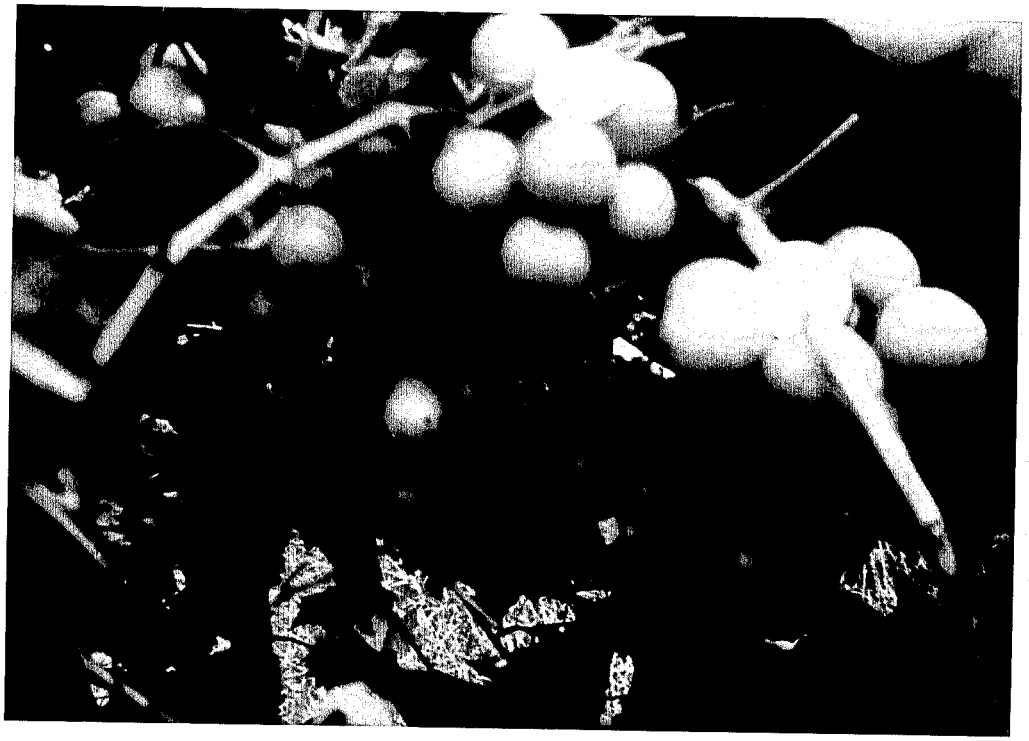

* * * * *